(12) United States Patent
Wu et al.

(10) Patent No.: US 7,918,798 B2
(45) Date of Patent: Apr. 5, 2011

(54) BONE EXAMINATION APPARATUS AND METHOD

(75) Inventors: Yu-Min Wu, Taipei County (TW);
Chih-Hsiung Yu, Taoyuan (TW);
Hsiao-Cheng Lin, Hsinchu (TW)

(73) Assignee: Quanta Computer Inc., Kuei Shan Hsiang, Tao Yuan Shien (TW)

( * ) Notice: Subject to any disclaimer, the term of this patent is extended or adjusted under 35 U.S.C. 154(b) by 567 days.

(21) Appl. No.: 12/071,539

(22) Filed: Feb. 22, 2008

(65) Prior Publication Data

US 2009/0082667 A1 Mar. 26, 2009

(30) Foreign Application Priority Data

Sep. 20, 2007 (TW) ................................ 96135065 A

(51) Int. Cl.
*A61B 8/00* (2006.01)
*A61H 1/00* (2006.01)
(52) U.S. Cl. ........ 600/449; 600/552; 600/437; 600/453; 601/84
(58) Field of Classification Search .................. None
See application file for complete search history.

(56) References Cited

U.S. PATENT DOCUMENTS

| | | | | |
|---|---|---|---|---|
| 3,477,422 A * | 11/1969 | Selle et al. | ..................... | 600/552 |
| 4,754,763 A * | 7/1988 | Doemland | ..................... | 600/552 |
| 4,926,870 A | 5/1990 | Brandenburger | | |
| 5,368,044 A * | 11/1994 | Cain et al. | ..................... | 600/552 |
| 5,836,876 A * | 11/1998 | Dimarogonas | ............... | 600/407 |
| 6,077,224 A * | 6/2000 | Lang et al. | ..................... | 600/437 |
| 6,095,979 A * | 8/2000 | Ohtomo | ......................... | 600/449 |
| 2002/0161300 A1 * | 10/2002 | Hoff et al. | ..................... | 600/449 |
| 2004/0127793 A1 * | 7/2004 | Mendlein et al. | ............. | 600/442 |
| 2005/0015002 A1 * | 1/2005 | Dixon et al. | ................... | 600/407 |
| 2005/0197576 A1 * | 9/2005 | Luo et al. | ...................... | 600/438 |
| 2008/0132775 A1 * | 6/2008 | Engan et al. | .................. | 600/407 |

FOREIGN PATENT DOCUMENTS

| | | |
|---|---|---|
| JP | 2005102716 | 4/2005 |
| TW | 144806 | 8/1989 |
| TW | 492859 | 3/1999 |

OTHER PUBLICATIONS

Office Action in related Chinese Application dated Dec. 25, 2009.
Translated Paragraphs [0004] and [0026]-[0029] of the Specification of JP2005-102716.
U.S. Appl. No. 60/071,461, filed Jan. 14, 1998, Goll et al.

(Continued)

*Primary Examiner* — Unsu Jung
*Assistant Examiner* — Lawrence N Laryea
(74) *Attorney, Agent, or Firm* — Thomas, Kayden, Horstemeyer & Risley, LLP

(57) ABSTRACT

The invention discloses a bone examination apparatus which includes a shaking module, a multi-mode ultrasonic detecting module, and a processing module. The shaking module is disposed close to a distal end of an examinee's femur, for inputting a shaking signal to the distal end. The multi-mode ultrasonic detecting module is disposed close to a near end of the examinee's femur, for detecting the shaking signal through the examinee's femur at the near end and generating a detecting signal. Additionally, the processing module is connected to the shaking module and the multi-mode ultrasonic detecting module respectively, for determining the examinee's bone density in accordance with the shaking signal, the detecting signal, and a first criterion.

16 Claims, 4 Drawing Sheets

OTHER PUBLICATIONS

Study of Total Hip Prosthesis Loosening by Hilbert Huang Transform and Fast Fourier Transform (Academic Thesis of the Master's degree, Department of Biomedical Engineering of Chung Yuan Christian University, Mei-Fen Chen, Jun. 2003, p. 2-3, 27 and 37) Please note that the English abstract is included in the thesis.

* cited by examiner

BONE EXAMINATION APPARATUS AND METHOD

BACKGROUND OF THE INVENTION

1. Field of the Invention

The present invention relates generally to a bone examination apparatus and method, and more particularly, to a bone examination apparatus and method for examining the bone density of femur and the loosening status of hip joint.

2. Description of the Prior Art

Bone is an important organ of human body. It can support our body, protects other organs, performs hematopoiesis, and adjusts minerals. However, with the ever-increasing pressure in hectic modern life, people nowadays take unbalanced nutrients and lack enough exercises, thus their bone quality is descended. Moreover, the bone density of human beings approaches the peak at about 30 years of age, and flows away by about 0.3 to 2% every year. Therefore, regular examination to find, prevent and treat related problems such as osteoporosis, bone necrosis, or joint degeneration, as early as possible has been the key point of health examination.

To reach the goal of bone density examination, a number of equipment and methods have been developed, such as X-ray examination, single photon absorptiometry (SPA), dual photon absorptiometry (DPA), computed tomography (CT), dual energy X-ray absorptiometry (DEXA), and ultrasonic examination.

X-ray examination can only be applied to detect bone with calcium or fracture lower than 70%, so it is not sensitive and accurate enough. SPA or DPA apply the photon released by isotope to detect bone density. Because of the problem of half-life and stability, it is unusual to use SPA or DPA in examination. Moreover, although both the sensitivity and the accuracy of CT are very high, the irradiation and cost for examination make it hard to use CT for bone examination.

With the advantages of short examining time, no irradiation, and low cost, ultrasonic examination has been widely applied to examine bone density. For example, Taiwan patent publication no. 144806 discloses a method and apparatus for ultrasonic analysis of bone density in vivo, and Taiwan patent publication no. 492859 discloses an apparatus and method for ultrasonic bone assessment. However, ultrasonic examination can be easily effected by skin, muscle, or other soft tissues, so as to affect the accuracy of the examination.

Additionally, because of the advantages of low irradiation and small error, Dual-energy X-ray Absorptiometry (DEXA) has been the major equipment for bone density examination. However, DEXA needs a longer examination duration, and the volume of the equipment is giant, both limit the portability and popularity of it.

Therefore, it is necessary to develop a bone density examination equipment with certain accuracy, safety, and convenience.

SUMMARY OF THE INVENTION

Accordingly, one aspect of the present invention is to provide a bone examination apparatus and method, and more particularly, to a bone examination apparatus and method for examining the bone density of femur and the loosening status of hip joint.

According to a preferred embodiment, the bone examination apparatus of the invention includes a shaking module, a multi-mode ultrasonic detecting module, and a processing module. The shaking module is disposed close to a distal end of an examinee's femur, for inputting a shaking signal to the distal end. The multi-mode ultrasonic detecting module is disposed close to a near end of the examinee's femur, for detecting the shaking signal through the examinee's femur at the near end and for generating a detecting signal. The processing module is connected to the shaking module and the multi-mode ultrasonic detecting module respectively, for determining the bone density of the examinee in accordance with the shaking signal, the detecting signal, and a criterion.

According to another preferred embodiment, the bone examination method of the invention comprises the following steps: first of all, input a shaking signal to a distal end of an examinee's femur. Afterward, detect the shaking signal through the examinee's femur at a near end of the examinee's femur by multiple ultrasonic detecting modes, so as to generate a detecting signal. Finally, determine the bone density of the examinee in accordance with the shaking signal, the detecting signal, and a criterion.

The objective of the present invention will no doubt become obvious to those of ordinary skill in the art after reading the following detailed description of the preferred embodiment, which is illustrated in the various figures and drawings.

BRIEF DESCRIPTION OF THE APPENDED DRAWINGS

DETAILED DESCRIPTION OF THE INVENTION

The invention provides a convenient and safe bone examination apparatus and method.

Figure 1:
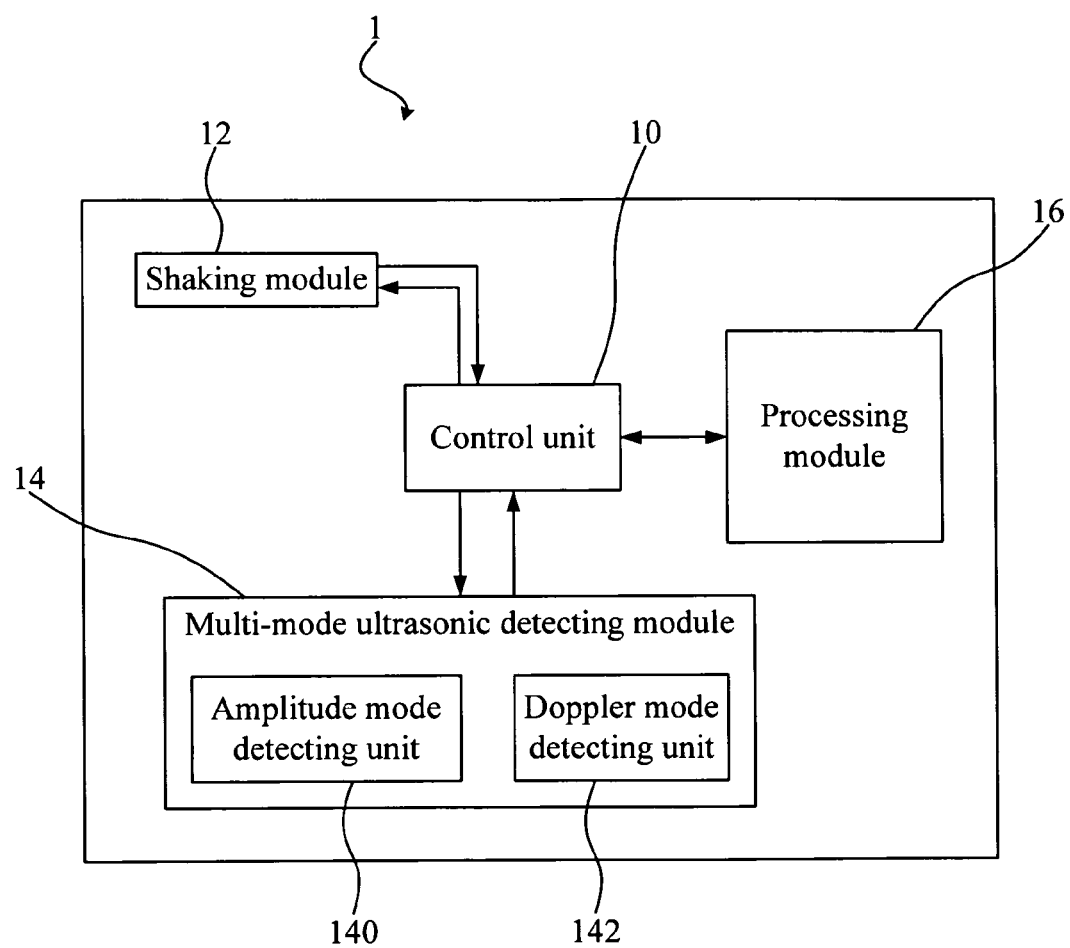
FIG. 1 illustrates a functional block of a bone examination apparatus of an embodiment of the invention.

Please refer to FIG. 1, which shows a functional block of a bone examination apparatus of an embodiment of the invention. As shown in FIG. 1, the bone examination apparatus 1 comprises a control unit 10, a shaking module 12, a multi-mode ultrasonic detecting module 14, and a processing module 16.

The control unit 10, such as a micro control unit (MCU), is connected to the shaking module 12, the multi-mode ultrasonic detecting module 14, and a processing module 16, for driving both the shaking module 12 and the multi-mode ultrasonic detecting module 14 in accordance with the driving signal transmitted by the processing module 16.

The shaking module 12 can be driven by the control unit 10 to generate the shaking signal. In practice, the shaking signal can be, but not limited to, longitudinal wave signal. Moreover, in practice, the resonance frequency of the shaking signal is in between 50~2,000 Hz.

The multi-mode ultrasonic detecting module 14 can detect the shaking signal, generated by the shaking module 12 after being driven by the control unit 10, through an examinee's femur and generates a corresponding detecting signal. Furthermore, the multi-mode ultrasonic detecting module 14 can comprise an amplitude mode (A mode) detecting unit 140 and a Doppler mode detecting unit 142. The A mode detecting unit 140 can be used to detect the depth of the detecting signal, whereas the Doppler mode detecting unit can be used to detect the detecting signal with low frequency.

The processing module 16, such as a central processing unit, can be connected to the shaking module 12 and the multi-mode ultrasonic detecting module 14 through the control module 10, for determining the bone density of the examinee in accordance with the shaking signal from the shaking module 12, the detecting signal from the multi-mode ultrasonic detecting module 14, and a first criterion. In practice, the processing module 16 generates a damping factor in accordance with the shaking signal and the detecting signal, and the first criterion comprising that when the damping factor is smaller, the bone density of the examinee is higher.

Furthermore, the processing module 16 can determine the loosening level of the hip joint of the examinee in accordance with the detecting signal and a second criterion. Because resonance happens easier when the hip joint is loosening, the second criterion can be acquired base on the harmonic amplitude or fundamental amplitude of the detecting signal. For example, the second criterion can define that when the harmonic amplitude of the detecting signal is larger than 50% of the fundamental amplitude, the examinee's hip joint is loosening. Moreover, the second criterion can also define that when a spectrum of the detecting signal comprises at least five harmonic waves, the examinee's hip joint is loosening. Additionally, the second criterion can comprise that when the detecting signal comprises at least two resonance frequencies, the examinee's hip joint is loosening. Practically, the processing module 16 can do Fourier transform on the detecting signal and then process the above-mentioned determination.

Particularly, when the bone examination apparatus is used for detecting the bone density, the shaking signal generated by the shaking module 12 is preferably a shaking signal with a fixed frequency. On the contrary, when the bone examination apparatus is used for detecting the loosening level of the hip joint, the shaking signal generated by the shaking module 12 is preferably a chirp signal with a range of frequencies.

Figure 2A:
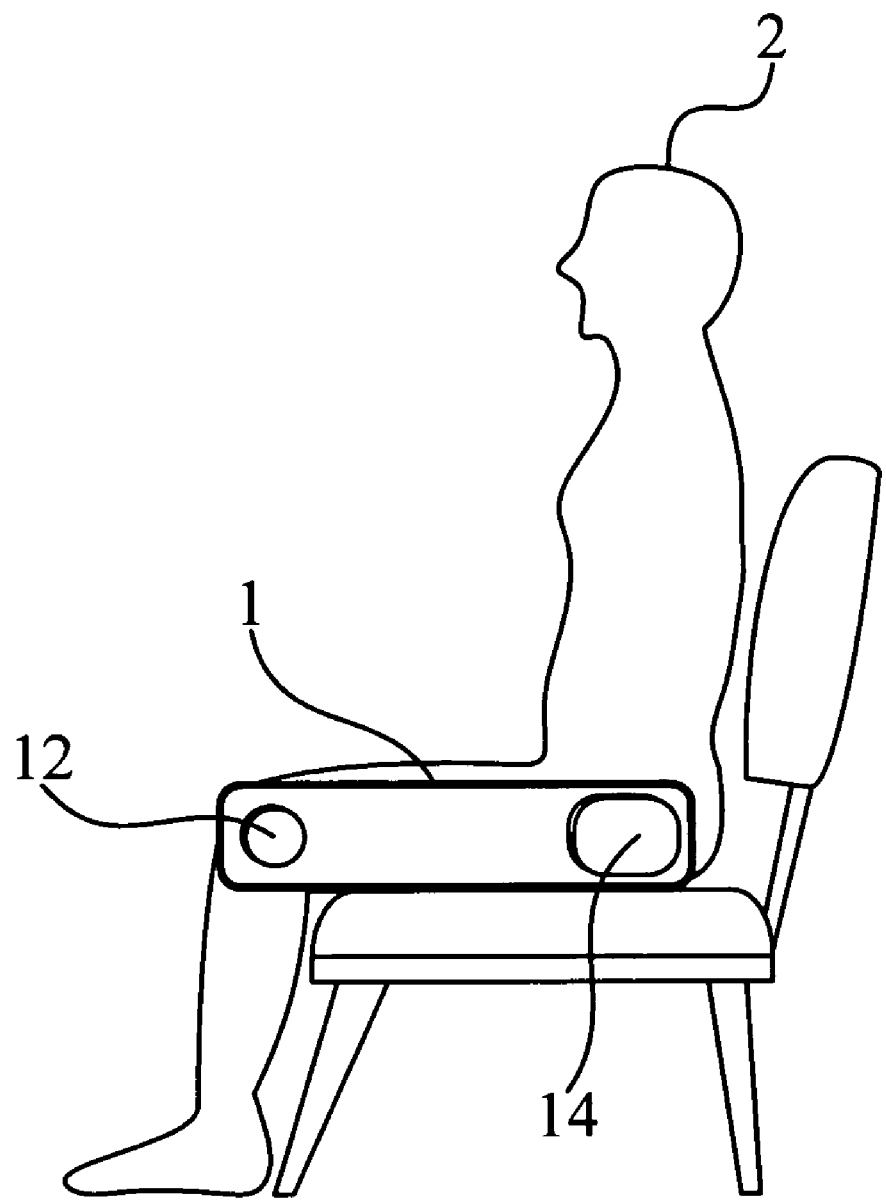
FIG. 2A illustrates a diagram of the bone examination apparatus of the invention to examine an examinee.

Please refer to FIG. 2A, which illustrates a diagram of the bone examination apparatus of the invention to examine an examinee. As shown in FIG. 2, the examinee 2 is sitting down to receive the examination. Certainly, in practice, the examinee 2 can optionally adjust his or her poses to receive the examination. For example, when the examinee 2 is confined to bed, he or she can receive the examination in a lying position.

Figure 2B:
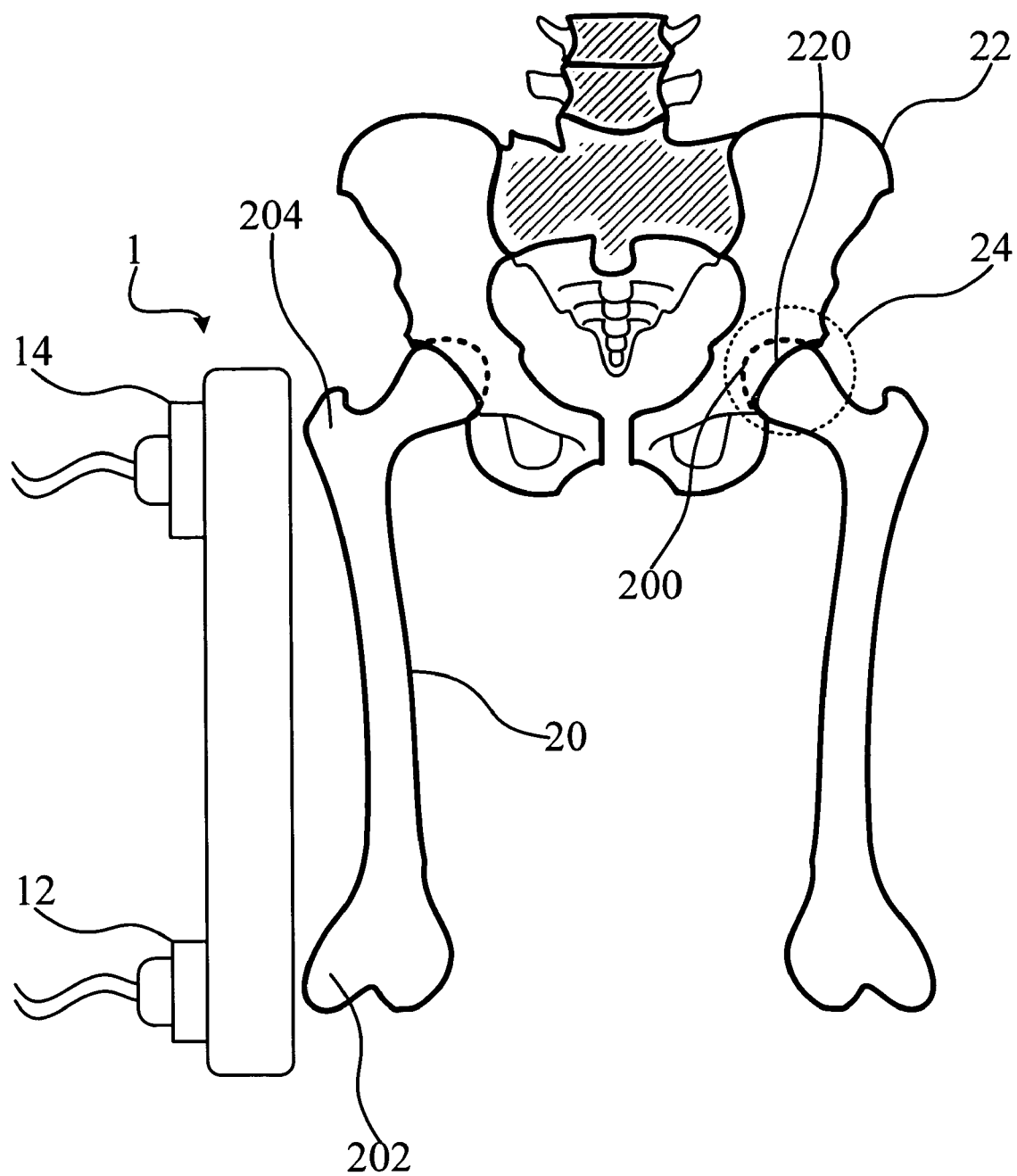
FIG. 2B illustrates the relationship between the bone examination apparatus of the invention and the bones of the examinee.

Furthermore, as shown in FIG. 2A, the shaking module 12 of the bone examination apparatus 1 of the invention is disposed close to the knee of the examinee 2. Please refer to FIG. 2B, which illustrates the relationship between the bone examination apparatus of the invention and the bones of the examinee. As shown in FIG. 2B, the Acetabulum 220 of the Hipbone 22 can contain the Femoral head 200 of the near end of the Femur 20 to form the hip joint 24.

During the examination, the shaking module 12 of the bone examination apparatus 1 of the invention is preferably disposed close to a distal end of an examinee's femur 20, and more preferably disposed close to the Lateral Epicondyle 202 of the femur 20. Additionally, as shown in FIGS. 2A and 2B, the multi-mode ultrasonic detecting module 14 of the bone examination apparatus 1 of the invention is disposed close to the bottom of buttocks of the examinee 2, preferably close to the near end of the femur 20, and more preferably close to the Great Trochanter 204 of the femur 20 to detect the shaking signal through the examinee's femur 20 more directly and generate a detecting signal.

Figure 3:
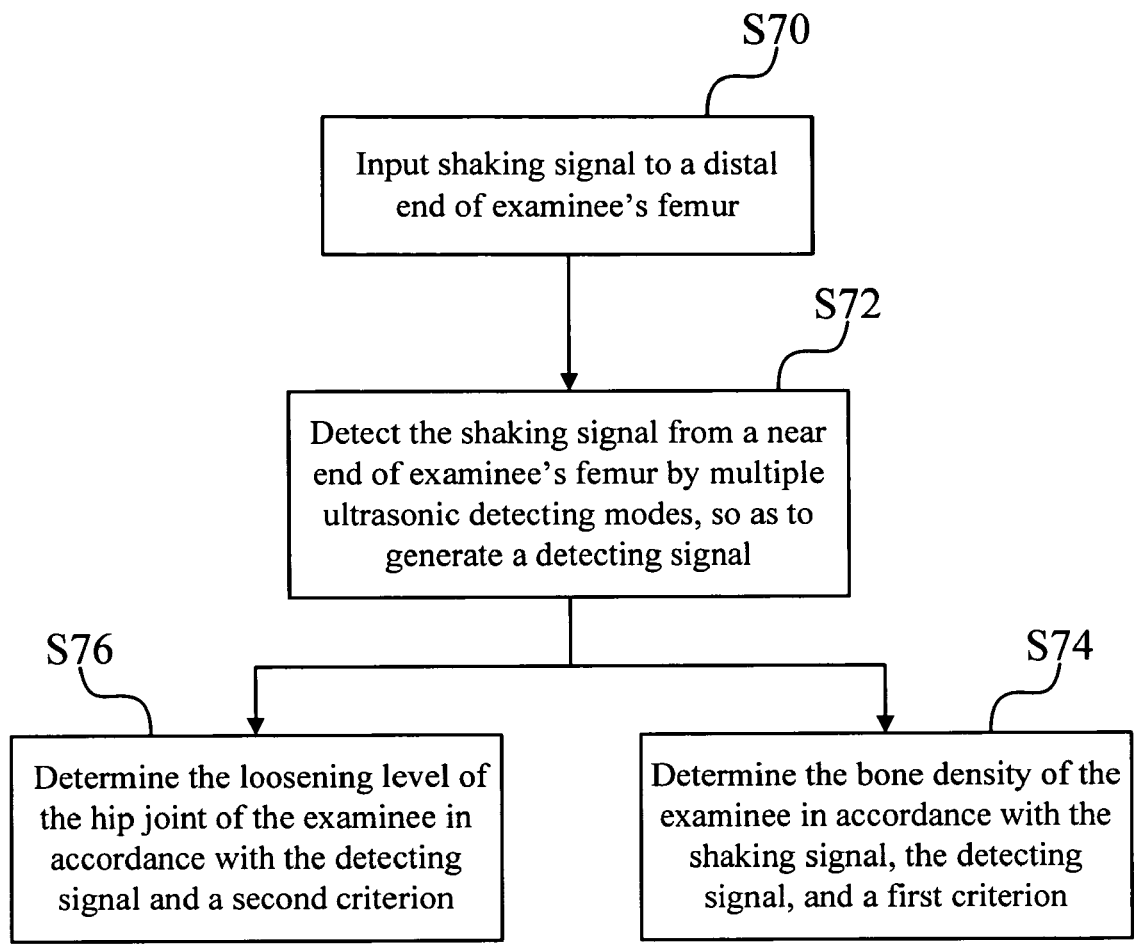
FIG. 3 shows the flow chart of a bone examination method of an embodiment of the invention.

Please further refer to FIG. 3, which shows the flow chart of a bone examination method of an embodiment of the invention. As mentioned above, the bone examination method of the invention can be applied for determining the bone density and loosening level of the hip joint of the examinee at the same time. As shown in FIG. 3, the bone examination method comprises the following steps of:

First of all, in step S70, input a shaking signal to a distal end of an examinee's femur. Practically, the resonance frequency of the shaking signal is between 50~2,000 Hz. Moreover, the shaking signal can be inputted to the Lateral Epicondyle (202, FIG. 2B) of the femur of the examinee.

Afterward, in step S72, detect the shaking signal through the examinee's femur at a near end of the examinee's femur by multiple ultrasonic detecting modes, so as to generate a detecting signal. In practice, the ultrasonic detecting modes can include, but not limited to, amplitude mode or Doppler mode. Moreover, in step S72, the shaking signal can be detected from the Great Trochanter (204, FIG. 2B) of the femur of the examinee.

Finally, in step S74, determine the bone density of the examinee in accordance with the shaking signal from the shaking module 12, the detecting signal from the multi-mode ultrasonic detecting module 14, and a first criterion. In practice, a damping factor can be generated in step S74 based on the shaking signal and the detecting signal. Moreover, the first criterion comprises that when the damping factor is smaller, the bone density of the examinee is higher.

Furthermore, as shown in FIG. 3, the bone examination method can comprise step S76, determine the loosening level of the hip joint of the examinee in accordance with the detecting signal and a second criterion. In practice, the second criterion can define that when the harmonic amplitude of the detecting signal is larger than 50% of the fundamental amplitude, the examinee's hip joint is loosening. Moreover, the second criterion can also define that when a spectrum of the detecting signal comprises at least five harmonic waves, the examinee's hip joint is loosening. Additionally, the second criterion can define that when the detecting signal comprises at least two resonance frequencies, the examinee's hip joint is loosening.

Please note that the above-mentioned first criteria and second criteria are only used for illustrating but not limiting the invention. In other words, the criteria can optionally be adjusted.

To sum up, the bone examination apparatus and method can effectively and rapidly estimate bone density and the loosening level of hip joint of an examinee at the same time. Except for providing information for the examinee to know his or her bone density, the results of the invention can further provide the basis for the doctor to prescribe suitable treatment. Moreover, because the invention applies the low-frequency shaking method, the damage to the examinee's body is smaller. Additionally, the bone examination apparatus has the advantages such as short examining time, high level of safety, low cost, and high portability.

Although the present invention has been illustrated and described with reference to the preferred embodiment thereof, it should be understood that it is in no way limited to the details of such embodiment but is capable of numerous modifications within the scope of the appended claims.

What is claimed is:

1. A bone examination apparatus for detecting bone density and loosening level of a hip joint, comprising:
 a shaking module, configured to be disposed close to a distal end of a femur of an examinee, for inputting a shaking signal to the distal end, wherein when detecting the bone density, the shaking signal generated by the shaking module is a shaking signal with a fixed frequency, when detecting the loosening level of the hip joint, the shaking signal generated by the shaking module is a chirp signal with a range of frequencies;

a multi-mode ultrasonic detecting module, configured to be disposed close to a near end of the examinee's femur, for detecting the shaking signal from the near end of the examinee's femur and generating a detecting signal, wherein the multi-mode ultrasonic detecting module comprises an amplitude mode (A mode) detecting unit and a Doppler mode detecting unit, the amplitude mode (A mode) detecting unit detects a depth of the shaking signal in the near end of the examinee's femur, and the Doppler mode detecting unit detects the shaking signal with low frequency at the depth thereof; and a processing module, connecting to the shaking module and the multi-mode ultrasonic detecting module respectively, for wherein the processing module is configured to determine the bone density and the loosening level of a hip joint of the examinee in accordance with the shaking signal, the detecting signal, and a criterion.

2. The bone examination apparatus of claim 1, wherein the processing module further generating a damping factor in accordance with the shaking signal and the detecting signal, and the criterion comprising that when the damping factor is smaller, the bone density of the examinee is higher.

3. The bone examination apparatus of claim 1, wherein the criterion comprises that when a harmonic amplitude of the detecting signal is larger than 50% of a fundamental amplitude, the examinee's hip joint is loosening.

4. The bone examination apparatus of claim 1, wherein the criterion comprises that when a spectrum of the detecting signal comprises at least five harmonic waves, the examinee's hip joint is loosening.

5. The bone examination apparatus of claim 1, wherein the criterion comprises that when the detecting signal comprises at least two resonance frequencies, the examinee's hip joint is loosening.

6. The bone examination apparatus of claim 1, wherein the distal end is a Lateral Epicondyle of the femur of the examinee.

7. The bone examination apparatus of claim 1, wherein the near end is a Great Trochanter of the femur of the examinee.

8. The bone examination apparatus of claim 1, wherein a resonance frequency of the shaking signal is in between 50~2,000 Hz.

9. A bone examination method for detecting bone density and loosening level of a hip joint, comprising the following steps:

(a) inputting a shaking signal to a distal end of a femur of an examinee, wherein when detecting the bone density, the shaking signal is a shaking signal with a fixed frequency, when detecting the loosening level of the hip joint, the shaking signal is a chirp signal with a range of frequencies;

(b) detecting the shaking signal from a near end of the examinee's femur inside the examinee's body by multiple ultrasonic detecting modes including amplitude mode for detecting a depth of the shaking signal in the near end of the examinee's femur, and a Doppler mode for detecting the shaking signal with low frequency at the depth thereof, so as to generate a detecting signal; and (c) determining the bone density and the loosening level of a hip joint of the examinee in accordance with the shaking signal, the detecting signal, and a criterion.

10. The bone examination method of claim 9, wherein step (c) further comprises the following step: (c1) generating a damping factor in accordance with the shaking signal and the detecting signal; wherein the criterion comprising that when the damping factor is smaller, the bone density of the examinee is higher.

11. The bone examination method of claim 9, wherein the criterion comprises that when a harmonic amplitude of the detecting signal is larger than 50% of a fundamental amplitude, the examinee's hip joint is loosening.

12. The bone examination method of claim 9, wherein the criterion comprises that when a spectrum of the detecting signal comprises at least five harmonic waves, the examinee's hip joint is loosening.

13. The bone examination method of claim 9, wherein the criterion comprises that when the detecting signal comprises at least two resonance frequencies, the examinee's hip joint is loosening.

14. The bone examination method of claim 9, wherein the distal end is a Lateral Epicondyle of the femur of the examinee.

15. The bone examination method of claim 9, wherein the near end is a Great Trochanter of the femur of the examinee.

16. The bone examination method of claim 9, wherein a resonance frequency of the shaking signal is in between 50~2,000 Hz.

* * * * *